United States Patent [19]

Manders

[11] Patent Number: 4,574,780

[45] Date of Patent: Mar. 11, 1986

[54] TISSUE EXPANDER AND METHOD

[76] Inventor: Ernest K. Manders, 1 Timberline Pl., Hummelstown, Pa. 17036

[21] Appl. No.: 670,623

[22] Filed: Nov. 13, 1984

[51] Int. Cl.[4] .............................................. A61B 19/00
[52] U.S. Cl. ........................................ 128/1 R; 623/8
[58] Field of Search ..................... 128/1 R; 3/1, 36; 604/96–103

[56] References Cited

U.S. PATENT DOCUMENTS

| | | | |
|---|---|---|---|
| 1,643,289 | 9/1927 | Peglay | 604/96 |
| 3,852,832 | 12/1974 | McGhan et al. | 3/36 |
| 3,883,902 | 5/1975 | Lynch | 3/36 |
| 3,919,724 | 11/1975 | Sanders et al. | 3/36 |
| 3,924,634 | 12/1975 | Taylor | 604/96 |
| 4,157,085 | 6/1979 | Austad | 128/1 R |
| 4,190,040 | 2/1980 | Shulte | 128/1 R |
| 4,217,889 | 8/1980 | Radovan et al. | 128/1 R |
| 4,428,364 | 1/1984 | Bartolo | 128/1 |

OTHER PUBLICATIONS

McGhan Medical Corporation, Reconstructive Mammary Implant Article, Oct. 1977.
Dow Corning Wright, Silastic Percutaneous Skin Expander Article, Jan. 1983.

*Primary Examiner*—Dalton L. Truluck
*Attorney, Agent, or Firm*—Thomas Hooker

[57] ABSTRACT

A soft tissue expander device adapted to be implanted beneath a layer of skin and subcutaneous tissue and filled with fluid to differentially expand the overlying tissue including methods for differentially expanding soft tissue and treating male pattern baldness.

46 Claims, 15 Drawing Figures

TISSUE EXPANDER AND METHOD

This invention relates to an improved inflatable soft tissue expander device and method useful in plastic and reconstructive surgery. Expander devices are conventionally implanted beneath the skin and subcutaneous tissue and then injected with a fluid to expand the overlying tissue. The device is then drained and surgically removed and the enlarged overlying tissue is surgically severed from surrounding tissue except at one edge to form an expanded tissue flap. The flap is applied to an adjacent recipient area larger than the area of the tissue overlying the device before expansion.

Conventional tissue expander devices as shown in Radovan et al U.S. Pat. No. 4,217,889, are formed from a biocompatible silicone elastomer and include a flexible non-extensible base with an overlying flexible cover bonded to the periphery of the base to define a sealed chamber between the cover and base. The area of the cover is greater than the area of the base so that when the device is collapsed the cover is folded on top of the base. The device includes an inlet port permitting hypodermic needle injection of a standard saline solution into the chamber following implantation of the device beneath the skin and subcutaneous tissue. Injection of the fluid into the chamber forces the cover above the base thereby uniformally expanding the overlying soft tissue and forming a uniformally expanded flap for subsequent application to an adjacent recipient area.

During expansion the overlying skin and subcutaneous tissues act as an elastic membrane and are expanded in response to the pressure exterted on them by the cover as solution is injected into the chamber. The overlying tissue expands above the entire base toward a generally domed shape independent of the shape of the base. Conventional bases are circular, oval and rectangular in shape. This type of tissue expansion forms a rounded generally uniform length flap as measured outwardly from the attached flap base.

The generally uniform length flap is suitable for many surgical procedures. There are other procedures, however, which require or would benefit from a non-uniform length flap. This type of flap is particularly useful when the expanded flap is applied to a non-planar or non-uniform length recipient area. For example, non-uniform length flaps may be used to advantage to reconstruct the scalp or in forming breast mound restorations.

The ability to expand soft tissue overlying an implanted expansion device differentially and form a differential width flap in accordance with the needs of the given surgical procedure would greatly enhance the usefulness of the expansion procedure and reduce or eliminate the need to gather and surgically fit an expanded flap to the reguirements of a given recipient area.

The disclosed expander device and method form differentially expanded tissue flaps. Differentially expanded flaps may be formed in two steps, the first step expanding the entire soft tissue overlying the expander device base and the second step expanding a portion only of the previously expanded overlying tissue. The differentially expanded flap includes a first portion which has been expanded only during the first step and a second portion expanded by both steps, the second portion having a width greater than that of the first portion.

One expander device used to form a differentially expanded tissue flap is similar to the conventional expander as shown in U.S. Pat. No. 4,217,889 but is provided with an improved cover having a first limited expansion portion secured to and overlying part of the base and a second differential expansion portion joined to the first portion and joined to and overlying a second part of the base. Following implantation of the expander device beneath the skin and subcutaneous tissue saline solution is injected into the device through an inlet port. The port may be remote from the base and cover as in U.S. Pat. No. 4,217,889 or may be provided in the relatively inexpandable portion of the cover.

As the saline solution fills the chamber between the cover and base the cover is forced upwardly away from the base and expands the overlying tissue. Initial injection of saline solution uniformally expands the overlying tissue. The expansion is controlled by the elastic properties of the overlying tissue. Both portions of the cover are raised above the base essentially uniformly until the limited expansion portion is extended and becomes taut. Expansion to this stage is the same as in a conventional expander device with a chamber cover having uniform expansion properties.

Further injection of saline solution into the chamber expands the weak differential expansion portion of the cover without appreciably further expanding the strong limited expansion portion of the cover. Such injection continues to stretch and expand the tissue overlying the differential expansion portion of the cover without further expanding the tissue overlying the limited expansion portion of the cover. In this manner, the tissue overlying the expander is differentially expanded in two steps to form a flap having a desired shape. Expansion devices may be specially constructed to form flaps having particularly useful shapes so that a surgeon may expand overlying tissue as required to form a specialized flap meeting the requirements of the particular procedure.

Differential expander devices are particularly useful in expanding the hair bearing portions of the scalp to either side of the central bald area formed by male pattern baldness. The expanded flaps have a greater anterior than posterior width. Following differential expansion the flaps are applied to cover the central bald area. The temporal hair-bearing tissue is differentially expanded anteriorly permitting the hair-bearing flap to be applied forwardly across the top of the skull to create a desired forward hairline.

Treatment of male pattern baldness by differential expansion represents a considerable improvement over conventional treatment of male pattern baldness by transplantation of hair plugs, serial excision of bald scalp tissue and transposition of narrow hair-bearing flaps. These procedures are costly, long in duration and frequently unsuccessful.

Other objects and features of the invention will become apparent as the description proceeds, especially when taken in conjunction with the accompanying drawings illustrating the invention, of which there are three sheets and six embodiments.

Figure 1:
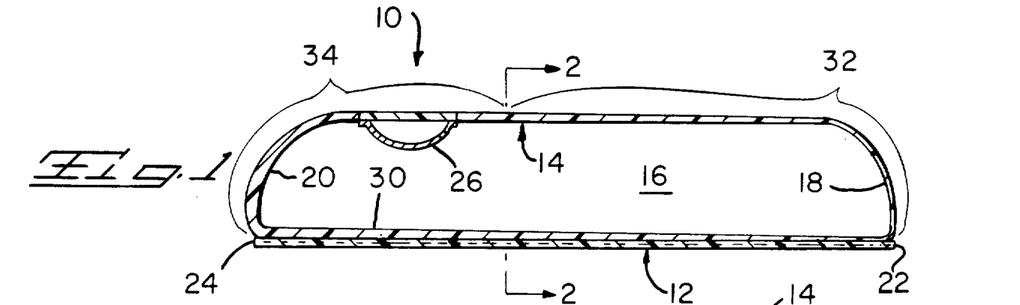
FIG. 1 is a sectional view taken along the length of an improved soft tissue expander device according to the invention.
Figure 2:
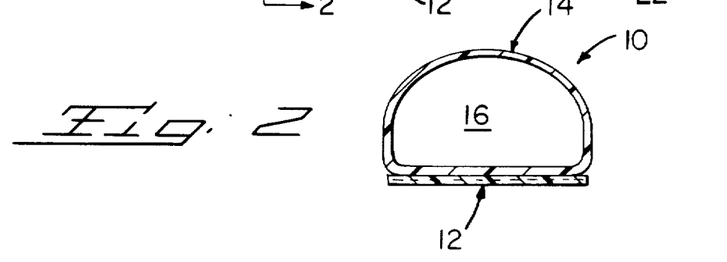
FIG. 2 is a sectional view taken along line 2—2 of FIG. 1.
Figure 3:
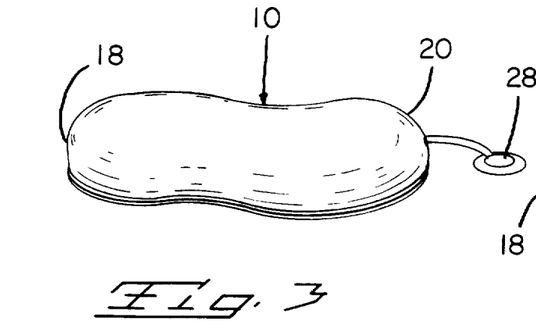
FIG. 3 is a perspective view of a device similar to the device of FIG. 1 with the interior chamber filled with a saline solution and the cover taut but without differential expansion.
Figure 4:
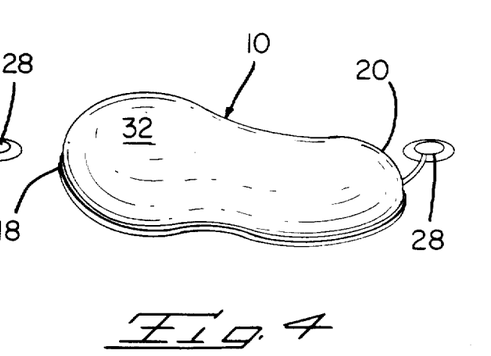
FIG. 4 is a view like that of FIG. 3 showing the device with additional saline solution injected into the chamber and the expandable portion of the cover expanded relative to the inexpandable portion of the cover.

FIGS. 1 and 2 illustrate a device 10 for differential expansion of soft tissue including a flexible base 12 having a width indicated in FIG. 2 and rounded ends as in FIGS. 3 and 4. Cover 14 overlies the base. The base and cover comprise a continuous flexible wall defining a liquid impervious chamber 16 within the interior of the device. The base may be formed from a sheet of reinforced silicone elastomer material with the reinforcement assuring that the base is dimensionally stable during soft tissue expansion. A reinforced base facilitates insertion of the device into a pocket below the tissue to be expanded, helps control the width of the cover and distributes stress to the underlying tissue. In some applications the base need not be reinforced, particularly where underlying bone supports the expander device. For example, a reinforced base is not required when the expander device is used to expand tissue overlying the hard cranium. The cover may be formed from reinforced or unreinforced silicone elastomer. Both the cover and base may be formed from Silastic brand elastomer marketed by Dow Corning Corporation of Midland, Mich.

Figure 5:
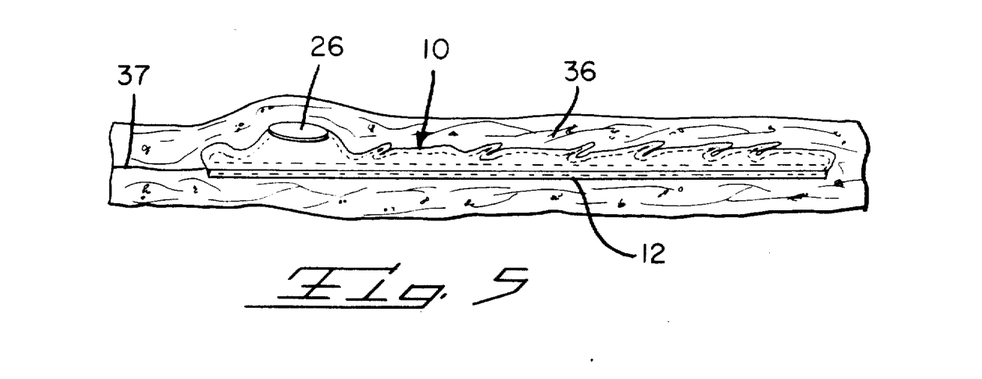
FIG. 5 is a sectional view illustrating a deflated expander device implanted beneath a soft tissue skin and subcutaneous layer.

FIGS. 1 and 2 illustrate the expansion device 10 with chamber 16 inflated until the cover 14 is taut but not dimensionally expanded. In this position the cover has a uniform transverse cross section along the length of the base with smooth, rounded ends 18 and 20 joining the rounded ends 20 and 22 of the flat base 12. A fluid inlet port 26 is provided in cover 14 adjacent end 20 to permit hypodermic needle injection of a saline solution into the chamber 16 during the expansion procedure. If desired, the device 10 may be provided with an external inlet port 28 as shown in FIGS. 3 and 4 and in U.S. Pat. No. 4,217,889. The area of the cover 14 is greater than the area of the base. When chamber 16 is empty the cover is folded and rests on the base as shown in FIG. 5.

The thickness of the cover 14 decreases from base end 22 around the exterior of the chamber to base end 20. The thickness of the cover away from the base is uniform in transverse cross section as indicated in FIG. 2. Port 26 is located in a relatively thick portion of the cover.

The cover 14 may be manufactured by first creating a form having an exterior shape conforming to the interior shape of the cover as shown in FIG. 1 and then dipping the form in liquid silicone elastomer in a manner to form a silicone elastomer envelope surrounding the form and having the desired tapered thickness. The form may be attached to a suitable support at an area subsequently cut out for attachment of the port 26. After dipping and drying of the elastomer to form the continuous envelope the form may be crushed and withdrawn through the support opening. The bottom 30 of the continuous envelope is suitably bonded to the nonextensible base 12 as shown. The tapered thickness of bottom 30 of the envelope forms no part of the invention. Manufacture is completed by securing a port 26 to the cover as illustrated.

FIGS. 3 and 4 illustrate a slightly different version of the device 10 with a tapered cover as in FIG. 1 and an exterior port 28. FIG. 3 illustrates the device filled with 300 cc of saline solution to make the cover taut without stretching either the thin differential expansion portion 32 of the cover or the relatively thick limited expansion portion 34 of the cover. Portion 32 extends from base end 22 around the cover end 18 and a distance along the cover toward base end 24. Portion 34 extends from portion 32 to base end 24. The taut device has an essentially uniform cross section along the length of the base as indicated in FIG. 2. See FIG. 1.

FIG. 4 illustrates the device of FIG. 3 after an additional 300 cc of fluid has been injected into chamber 16. The additional fluid elastically expands the relatively thin differential expansion cover portion 32. This portion expands, increases in area and assumes an increasingly bulbous shape. The shape of portion 32 becomes more nearly hemispheric as additional fluid is injected into the chamber. The strength of the silicone elastomer cover permits considerable expansion of the portion 32 without rupture.

Limited expansion portion 34 of the cover away from expandable portion 32 has an increased thickness and is stronger than portion 32. This portion is essentially dimensionally stable and does not expand beyond the taut position of FIG. 3. The inlet port is secured to cover portion 34 to assure that the cover—port connection is not unduly stressed as additional fluid is injected into the chamber. Further, by locating the inlet port in the limited expansion portion of the cover the surface of the differential expansion cover portion is kept smooth and can freely slide relative to the overlying tissue as it and the tissue expand.

As illustrated in FIG. 5, the collapsed device 10 of FIG. 1 is surgically implanted in tissue pocket beneath a patient's skin and subcutaneous tissue layer 36 with base 12 parelleling and facing away from the overlying soft tissue. The collapsed cover 14 has a greater area than the base and is folded against the base as shown. Port 26 faces the skin. The device may be inserted into the pocket through incision 37.

Figure 6:
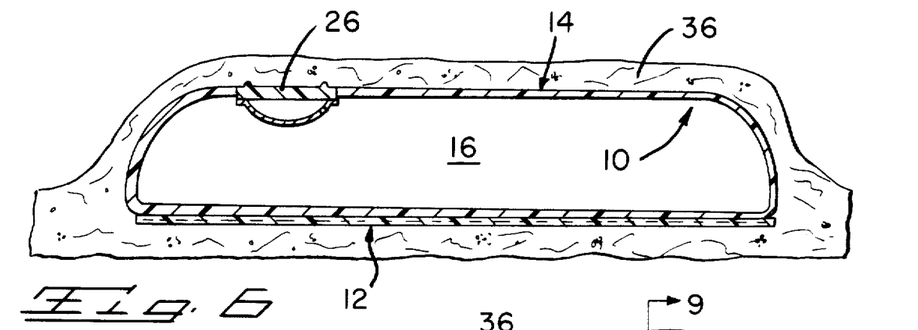
FIG. 6 is a sectional view similar to that of FIG. 5 showing the device filled with saline solution and with the cover taut as in FIG. 3.

FIG. 6 illustrates the expander device 10 of FIG. 5 after sufficient saline solution has been injected into the chamber 16 through port 26 to fill the chamber without stretching the cover. Both cover portions 32 and 34 are taut. The overlying layer of soft tissue 36 has been uniformally expanded along the length of the device. Expansion of the soft tissue 36 from the condition of FIG.

5 to the condition of FIG. 6 is controlled by the elastic properties of the tissue itself, independent of the properties of the unfolding cover as it assumes the position of FIGS. 1, 2 and 3 and becomes taut.

Figure 7:
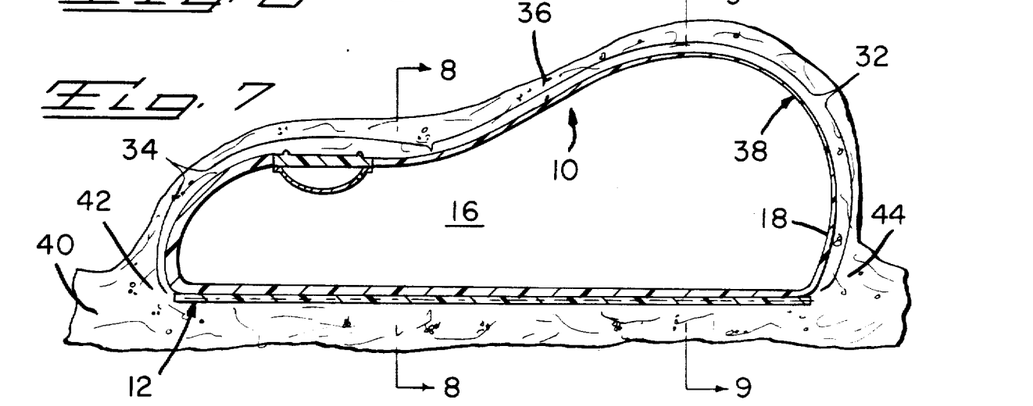
FIG. 7 is a sectional view like FIGS. 5 and 6 but with the cover and overlying tissue differentially expanded.
Figures 8, 9:
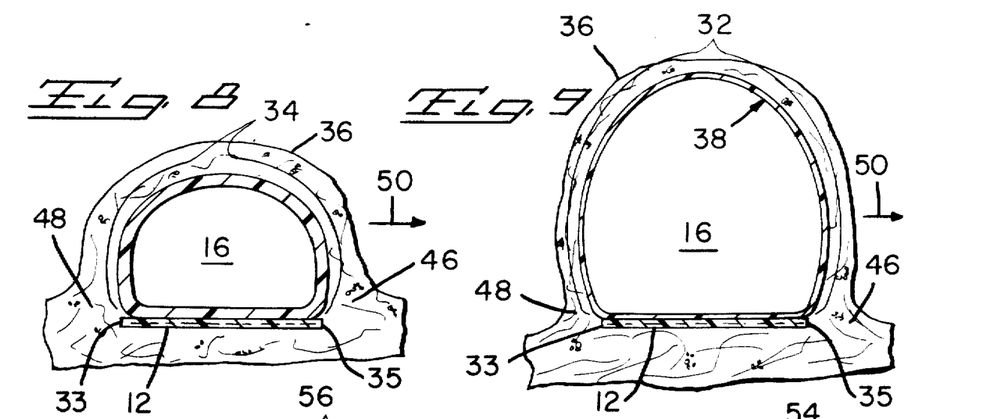
FIGS. 8 and 9 are sectional views taken respectively along lines 8—8 and 9—9 of FIG. 7.

Further injection of saline solution into the chamber 16 increases the pressure exerted against the entire cover 14. The thick, limited expansion cover portion 34 withstands the pressure without appreciable expansion. The thinner, differential expansion cover portion 32 expands in response to the increased pressure and assumes a bulbous, expanded area shape 38 as shown in FIGS. 4, 7 and 9. Shape 38 becomes more nearly spherical with injection of solution.

As the cover expands from the position of FIG. 6 to that of FIG. 7 the soft tissue 36 overlying cover portion 32 is stressed and expands with the cover. The portion of the soft tissue overlying the portion 34 of the cover is not expanded. As a result, injection of additional fluid into the chamber expands only the soft tissue overlying one end of the device 10. The net result of the expansion process is that the overlying soft tissue is differentially expanded with an additional benefit that the soft tissue overlying cover end 18 is expanded beyond the base as the cover portion 32 assumes bulbous shape 38. During expansion the cover is forced against the overlying tissue layer.

FIGS. 8 and 9 illustrates that the cover portions 32 and 34 extend circumferentially around the cover from edge 33 to edge 35 of the base.

Following full expansion of device 10 as shown in FIG. 7 and differential expansion of the overlying soft tissue 36, the surgeon withdraws the saline solution from chamber 16 and removes the device 10 from beneath the tissue. The expanded tissue shown in FIGS. 7, 8 and 9 is severed from the surrounding tissue 40 by incisions along edges 42, 44 and 46 while leaving the expanded tissue flap attached at edge or base 48. The flap has a length outwardly from the attached base 48 greater as measured along the tissue expanded by cover portion 32 than as measured along the tissue expanded by cover portion 34. The differentially expanded flap is extended in the direction of arrow 50 and applied to an adjacent recepient area in the manner and with the advantages previously described.

Figure 10:
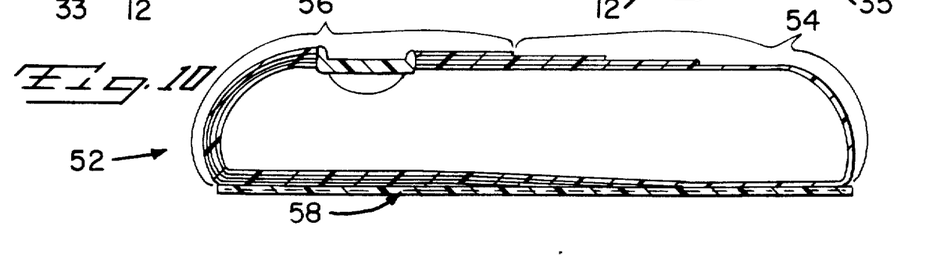
FIGS. 10, 11, 12 and 13 are views similar to the view of FIG. 1 illustrating further embodiments of the invention.

FIG. 10 illustrates a expansion device 52 similar to device 10 except that the cover is formed of a number of discrete bonded layers of silicone elastomer so that the thickness of the cover decreases in steps along the thin, differential expansion cover portion 54 and the thick limited expansion portion 56 has a uniform four layer thickness. These portions are secured to the periphery of base 58 like base 12.

Expander device 52 is implanted and expanded in the same manner as described in connection with device 10 to differentially expand an overlying layer of skin and subcutaneous tissue.

Figure 11:
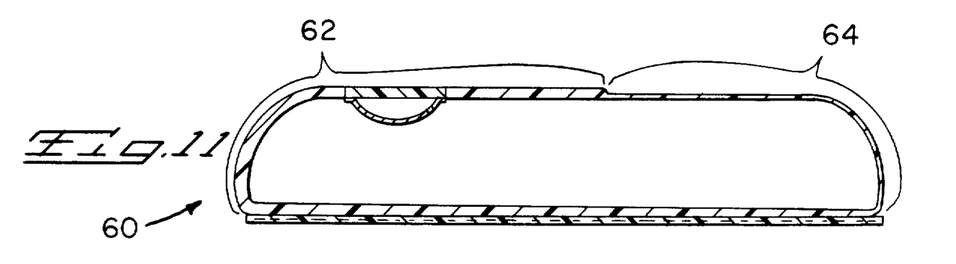
Figure 12:
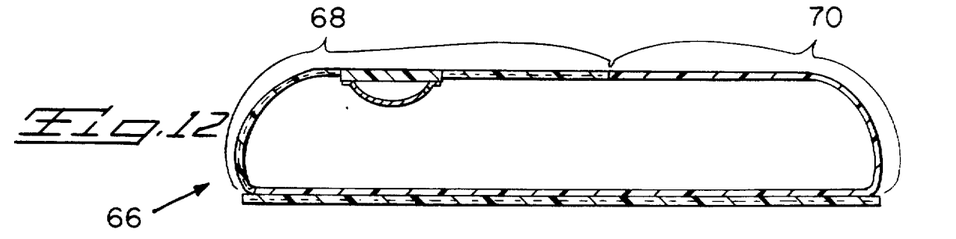

FIG. 11 illustrates an expansion device 60 similar to device 10 where the cover includes a thick uniform thickness silicone elastomer like portion 64 of device 60. Devices 60 and 66 are used to form differentially expanded soft tissue flaps in the same manner as described in connection with device 10.

Figure 13:
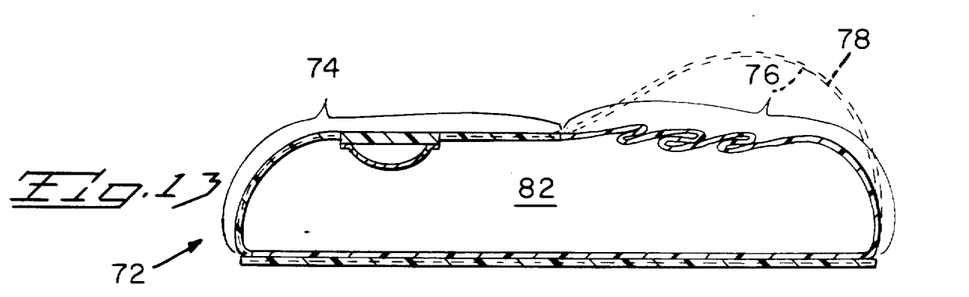

FIG. 13 illustrates device 72 similar to device 66 of FIG. 12 having a reinforced limited expansion cover portion 74 and a folded large area differential expansion portion 76 which may be freely expanded to assume a bulbous shape 78 as shown in dotted lines.

Device 72 is implanted beneath the layer of skin and subcutaneous tissue and expanded in the manner described in connection with device 10. The device 72 expands in the same manner as device 10 until the saline solution within the chamber 82 fully expands portion 74 and similarily expands the folded portion 76. As described in connection with device 10, expansion to this point is controlled by the elastic properties of the overlying tissue so that the two portions 74 and 76 expand together. Injection of further saline solution into the chamber 82 unfolds and expands portion 76 until it assumes the fully expanded bulbous shape 78, thus completing the differential expansion of the overlying soft tissue. Portion 74 does not expand beyond the portion of FIG. 13.

Portion 76 may be reinforced to assure that the cover assumes a known maximum shape when expanded. Alternatively, portion 76 may be formed from elastically expandable silicone elastomer so that additional saline solution may be injected into the chamber 82 to expand portion 76 sufficiently to meet the requirements of a given procedure. Additional solution may be introduced into the chambers of the other expander devices for further expansion of the cover portions 32, 54 64 and 70 if the surgeon determines the maximum length of the flap should be increased.

Figure 14:
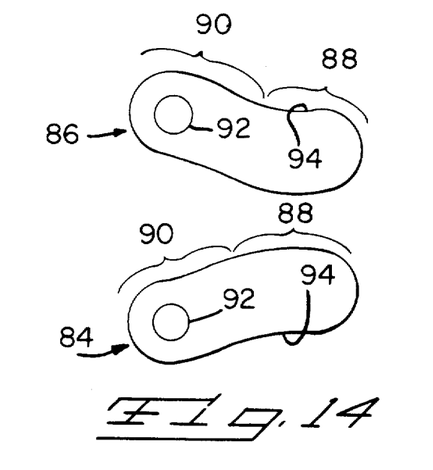
FIG. 14 is a top view of a pair of differential tissue expander devices useful in treating male pattern baldness.

FIG. 14 is a top plan view of two scalp expansion devices 84 and 86 used in the treatment of male pattern baldness. Devices 84 and 86 are generally similar to device 10 and include a base (not illustrated) and a cover including a differential expansion cover portion 88 at one end of the base and a limited expansion cover portion 90 at the other end of the base. An inlet port 92 is provided in each cover portion 90. Portions 88 and 90 and port 92 may be like the previously described portions and ports.

The devices 84 and 86 are symmetrical as viewed from above with each including a shallow recess 94 in the lower base edge of the device when the device is implanted beneath the scalp.

Figure 15:
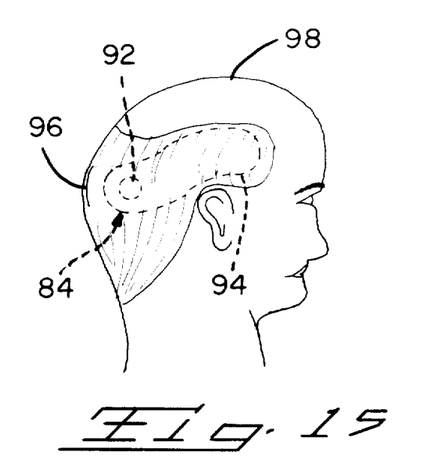
FIG. 15 is a side view illustrating the implantation of one of the expanders of FIG. 14 in the treatment of male pattern baldness.

Male pattern baldness is treated using devices 84 and 86 by making a short vertical incision 96 through the scalp at the center of the occiput and then forming two pockets beneath the scalp and subcutaneous tissue extending anteriorly to either side of the incision, past the occiput and into the temporal area above each ear. The pockets are carefully formed under the hair bearing scalp and below the typical male pattern bald area 98 shown in FIG. 14. Right hand device 84 is then implanted in the right hand pocket with recess 94 above the ear as illustrated and left hand device 86 is similarily implanted within the pocket formed on the left hand side of the head. The surgery is then completed in the conventional manner and incision 86 is sutured closed.

Both devices 86 and 84 are expanded by the injection of saline solution into ports 92, thereby differentially expanding the hair-bearing scalp overlying the cover portions 88 and 90 with the result that the hair-bearing temperal scalp overlying portions 88 is expanded considerably more than the hair-bearing occiputal scalp overlying portions 90.

Following differential scalp expansion and removal of the devices 84 and 86 the upper, anterior and posterior edges of the expanded scalp are severed from the adjacent scalp, the bald scalp area is removed and 98 the flaps are drawn around the head, joined at the center line and applied to the underlying tissue. The flaps are longer at the temporal area due to the differential expansion thereby permitting them to meet at the top of the head and completely restore the patient's hair. In the event the differential expansion cover portions 88 bulge forward of the adjacent base ends as shown in FIG. 7 the corresponding expansion of the overlying hair-bearing scalp may be carried anteriorly to provide a desired forward front hairline.

During expansion of the hair-bearing scalp the hair density is reduced somewhat, however, this is not noticable in practice. The surgical scars resulting from the elimination of male pattern baldness using devices 84 and 86 are located under hair or adjacent the hairline and concealed by the hair.

The area of hair-bearing temporal scalp available for expansion is frequently limited. In order to make maximum use of the available temporal hair the expansion device is preferrably positioned underneath as much of the available hair as possible. Expansion of the available temporal hair is facilitated by providing the shallow recesses 94 in the devices which enables them to be extended close to and around the ears.

Expansion devices are implanted in soft tissue a short distance below the skin. The underlying tissue supporting the base of the device is stronger than the overlying tissue so that injection of fluid into the cavity expands the cover outwardly with resultant differential soft tissue expansion. Depending upon the strength of the underlying support the base may be retained flat in the initial implant position or may be bowed inwardly during expansion. The support provided by underlying tissue means it is not essential to use a reinforced base in order to achieve differential soft tissue expansion. For instance, devices 84 and 86 used in treating male pattern baldness are implanted in pockets directly overlying the hard cranium so that the bases of these devices are firmly supported and injection of saline solution expands the cover portions as described even if the base is not reinforced. Likewise, an expansion device used to differentially expand a flap for breast mound reconstruction is supported by the rib cage and a device implanted in a buttock for expanding buttock tissue is supported by underlying muscle. The bases of these devices need not be dimensionally stable.

Covers of expansion devices according to the invention need not have a collapsed area greater than the area of the base. The area of the cover may be greater, equal to or less than the area of the base so long as the cover includes a limited expansion portion and a differential expansion portion underlying the skin and subcutaneous tissue.

The expansion devices illustrated herein all use covers with a single limited expansion portion and a single differential expansion portion so that the overlying tissue is expanded in two corresponding areas. The invention contemplates expanders with covers having two or more limited expansion or differential expansion portions in order to form flaps having more complicated differentially expanded shapes than illustrated. For instance, an expander may include an elongate base with a cover having a limited expansion portion adjacent one end of the base, a differential expansion portion over the middle of the base and a second limited expansion portion over the other end of the base. Injection of saline solution and expansion using such a device would form a flap with two single expanded portions to either side of a differentially expanded tissue portion. Devices having other combinations of limited and differential expansion cover portions may be provided as required.

The differentially expanded flaps described herein are attached to the surrounding tissue and are extended and applied to adjacent recipient areas. It is not necessary that a differentially expanded flap be applied in this way. In some applications, the flap may be completely removed from the surrounding tissue and applied to a remote site. As an example, a differentially expanded flap may be formed by expanding buttock tissue, which may be transferred to the lower leg or foot.

The bases of the disclosed devices are all formed of flat sheet material. Bases may be curved or may have one or more sidewalls extending upwardly toward the cover when the device is taut, that is before differential tissue expansion. Base sidewalls increase total tissue expansion.

While I have illustrated and described preferred embodiments of my invention, it is understood that they are capable of modification, and I therefore do not wish to be limited to the precise details set forth, but desire to avail myself of such changes and alterations as fall within the purview of the following claims.

What I claim as my invention is:

1. A soft tissue expander device comprising a flexible base and an expandable cover joined to the periphery of the base to define a fluid tight chamber between the cover and base, a fluid injection port communicating with the interior of the chamber for admitting fluid into the chamber to expand the cover, the cover including a first limited expansion portion expandable by initial fluid injected through the port and into the chamber from a collapsed position overlying the base to a taut position a distance above the base and a differential expansion portion adjacent said limited expansion portion expandable by said initial injected fluid from a collapsed position overlying the base said distance above the base, said limited expansion portion including limiting means preventing further expansion of such portion beyond said taut position by fluid injected into the chamber in addition to the initial injected fluid and said differential expansion portion including expansion means permitting further expansion of such portion beyond said distance whereby upon implantation of the base and collapsed cover beneath a soft tissue layer of skin and subcutaneous tissue injection of fluid through the port and into the cavity first expands both the first and second cover portions together with the tissue overlying such portions said distance above the base and then expands the second cover portion together with the tissue overlying the second cover portion only beyond said distance to form a differentially expanded tissue flap.

2. A device as in claim 1 wherein each cover portion joins edges of the base and extends over the base between such edges.

3. A device as in claim 2 wherein the base is elongate and one of the portions is located at one end of the base.

4. A device as in claim 2 wherein the differential expansion portion is formed from an elastomer material and is bulbous in shape when such portion is fully expanded.

5. A device as in claim 4 wherein the differential expansion portion extends beyond the periphery of the base when fully expanded.

6. A device as in claim 1 wherein the cover is formed from an elastomer material.

7. A device as in claim 6 wherein the thickness of the differential expansion portion is essentially uniform.

8. A device as in claim 6 wherein the differential expansion portion is thinner than the limited expansion portion.

9. A device as in claim 8 wherein the thickness of the differential expansion portion decreases in a direction away from the limited expansion portion.

10. A device as in claim 6 wherein when the chamber is collapsed both portions are folded on top of the base, and both portions are taut following injection of initial fluid into the chamber.

11. A device as in claim 6 wherein both portions are folded on top of the base when the chamber is collapsed, and the limited expansion portion is taut and the differential expansion portion is folded following injection of initial fluid into the chamber.

12. A device as in claim 1 wherein the base of elongate, one cover portion overlies one end of the base and is joined to the side edges and one end thereof and the other portion extends across the base and is joined to the side edges of the base.

13. A device as in claim 1 wherein the port is secured to the limited expansion portion of the cover.

14. A device as in claim 1 wherein the base is dimensionally stable.

15. A device as in claim 6 wherein said base is elongate, said portions each overlie one end of the base, and the port is located in said limited expansion portion.

16. A device as in claim 15 including a shallow recess formed in one edge of the base adjacent the differential expansion portion whereby such device may be fitted within a pocket extending beneath hair bearing scalp with the limited expansion portion beneath occiputal scalp, the differential expansion portion beneath the temporal scalp and the recess fitted around the top of the ear.

17. An expander device adapted to be implanted beneath a soft tissue layer of skin and subcutaneous tissue and to differentially expand the overlying skin and tissue in two steps, comprising a flexible base and an expandable cover joined to the peripheral edge of the base to define a fluid tight chamber between the cover and base, a fluid injection port communicating with the interior of the chamber for admitting fluid into the chamber to expand the cover, the cover including a limited expansion portion and a differential expansion portion adjacent said limited expansion portion, said limited expansion portion including means preventing expansion beyond a taut position and the differential expansion portion including means permitting expansion beyond the taut position of the limited expansion portion, the device having a collapsed position when implanted with the cover overlying the base, a partially expanded position where fluid injected through the port and into the chamber expands the limited expansion portion of the cover a distance above the base to the taut position and the differential expansion portion of the cover a corresponding distance above the base, and a fully expanded position where further fluid injected through the port and into the chamber moves the differential expansion portion a further distance above the base beyond the limited expansion portion without further moving the limited expansion portion above the base whereby the skin and subcutaneous tissue overlying the cover are differentially expanded.

18. A device as in claim 17 wherein the base is elongate, the cover is formed from an elastomer material, and one cover portion overlies an end of the base.

19. A device as in claim 18 wherein the differential expansion portion is taut when the device is partially expanded.

20. A device as in claim 18 wherein the differential expansion portion is folded when the device is partially expanded.

21. A device as in claim 18 wherein the inlet port extends through the limited expansion portion.

22. A device as in claim 18 including a shallow recess formed in one edge of the base to permit the device to be implanted within a pocket below skin and subcutaneous tissue with the recess extending around an adjacent anatomical feature.

23. A device as in claim 22 wherein the recess is adjacent the differential expansion portion.

24. A surgical method of expanding and applying soft tissue by use of a soft tissue expander device having an expandable cover comprising the step of:
(a) Separating a layer of skin and subcutaneous soft tissue connected to surrounding skin and soft tissue from underlying support tissue to form a pocket;
(b) Placing a collapsed soft tissue expander device in the pocket with the cover of the device facing the separated tissue layer;
(c) Forcing the cover against the separated tissue to expand the tissue layer substantially uniformly away from the underlying tissue;
(d) Retaining a first portion of the cover in the expanded position and further forcing a second portion of the cover against the overlying portion of the separated tissue layer to further expand such overlying portion only;
(e) Collapsing and removing the soft tissue expander device from the pocket;
(f) Severing edges of the expanded layer from surrounding soft tissue to form a differentially expanded tissue flap; and
(g) Flattening and applying the tissue flap to a recipient area larger than the area of the separated layer.

25. The method of claim 24 including the steps of retaining one edge of the tissue flap connected to surrounding tissue, moving the flap away from the edge so that it overlies an adjacent recipient area and applying the flap to such area.

26. The method of claim 24 including the steps of completely severing the tissue flap from the surrounding soft tissue and applying the flap to a remote recipient area.

27. The method of treating male pattern baldness using a pair of soft tissue expander devices comprising the steps of:
(a) Forming pockets on both sides of the head between the skull and adjacent layers of hair-bearing occiputal and hair-bearing temporal scalp;
(b) Placing a soft tissue expander device in each pocket;
(c) Differentially expanding the devices in the pockets to form a differentially expanded hair-bearing scalp layer above each device with the length of the expanded temporal scalp being greater than the length of the expanded occiputal scalp;
(d) Collapsing and removing the soft tissue expander devices from the pockets;
(e) Removing the bald scalp area between the expanded scalp layers on each side of the head;
(f) Severing the upper, anterior and posterior edges of the expanded scalp layers from the adjacent scalp tissue to form flaps;

(g) Drawing the severed flaps upwardly around the head so that the flaps join at the center line and cover the former bald area; and (h) Applying the flaps to underlying tissue.

28. The method of claim 27 including the steps of expanding the temporal scalp layers anteriorly and drawing the flaps anteriorly to provide a forward hair line.

29. The method of claim 27 including the steps of forming a single vertical incision through the scalp at the center of the occiput, and separating hair-bearing scalp extending anteriorly to either side of the incision past the occiput and into the temporal area from underlying tissue prior to expansion.

30. The method of claim 29 including the steps of separating temporal hair-bearing scalp from underlying tissue closely surrounding the tops of the ears and expanding the temporal hair-bearing scalp located immediately above the ears.

31. A soft tissue expander device adapted to be implanted collapsed beneath a soft tissue layer of skin and subcutaneous tissue, the device comprising flexible wall means defining a fluid impervious chamber, and an injection port communicating with the interior of the chamber for admitting fluid into the chamber to expand the chamber, said wall means including an expandable cover in contact with the layer of skin and subcutaneous tissue when the device is implanted, the cover including a first limited expansion portion expandable by initial fluid injected through the port and into the chamber from a collapsed implantation position to a taut position above the collapsed position and a second differential expansion portion adjacent said limited expansion portion expandable by said initial injected fluid with the limited expansion portion above the collapsed implantation position, said limited expansion portion including limiting means preventing further expansion of such portion beyond said taut position by further fluid injected into the chamber in addition to the initial injected fluid and said differential expansion portion including expansion means permitting further expansion of such portion by said further fluid whereby fluid injected through the port and into a chamber of an implanted device first expands both the first and second cover portions together with the tissue overlying such portions and then further expands the second cover portion together with the tissue overlying the second cover portion only to form a differentially expanded tissue flap.

32. A device as in claim 31 wherein one cover portion extends across the cover.

33. A device as in claim 31 wherein said limited expansion portion extends across the cover.

34. A device as in claim 33 wherein the differential expansion portion is formed from an elastomer material and is bulbous in shape when such portion is fully expanded.

35. A device as in claim 31 wherein both cover portions extend across the cover.

36. A device as in claim 31 wherein the flexible wall means is elongate when collapsed and one of the portions is located at one end thereof.

37. A device as in claim 13 wherein the cover is formed of an elastomer material.

38. A device as in claim 37 wherein the thickness of the differential expansion portion is essentially uniform.

39. A device as in claim 37 wherein the differential expansion portion is thinner than the limited expansion portion.

40. A device as in claim 39 wherein the thickness of the differential expansion portion decreases in a direction away from the limited expansion portion.

41. A device as in claim 37 wherein when the device is collapsed both portions are folded, and both portions are taut following injection of initial fluid into the chamber.

42. A device as in claim 37 wherein when the device is collapsed both portions are folded, and the limited expansion portion is taut and the differential expansion portion is folded following injection of initial fluid into the chamber.

43. A device as in claim 31 wherein the device is elongate when collapsed, one cover portion is at one end of the device and the other cover portion is at the other end of the device and both cover portions extend across the cover.

44. A device as in claim 31 wherein the port is formed in the limited expansion portion of the cover.

45. A device as in claim 31 wherein the port is remote from the flexible wall means.

46. A device as in claim 31 wherein the wall means includes a dimensionally stable base.

* * * * *

UNITED STATES PATENT AND TRADEMARK OFFICE
CERTIFICATE OF CORRECTION

PATENT NO. : 4,574,780
DATED : March 11, 1986
INVENTOR(S) : Ernest K. Manders

It is certified that error appears in the above—identified patent and that said Letters Patent is hereby corrected as shown below:

In the Specification:

Column 3, line 56 change "20 and 22" to --22 and 24--.

Column 3, line 67 change "22" to --24--.

Column 3, line 68 change "20" to --22--.

Column 5, line 59 after "thick" insert a comma.

Column 5, line 60 after "thickness" insert a comma and change "64" to --62--.

Column 6, line 24 insert a comma between "54" and "64".

Column 6, line 65 change "and" to --at--.

In the Claims:

Claim 1, line 10 (column 8, line 32) before "differential" insert --second--.

Claim 12, line 1 (column 9, line 16) change "of" to --is--.

UNITED STATES PATENT AND TRADEMARK OFFICE
CERTIFICATE OF CORRECTION

PATENT NO. : 4,574,780
DATED : March 11, 1986
INVENTOR(S) : Ernest K. Manders

It is certified that error appears in the above-identified patent and that said Letters Patent is hereby corrected as shown below:

Claim 37, line 1 (column 12, line 16) change "13" to --31--.

Signed and Sealed this

Fifth Day of July, 1988

*Attest:*

DONALD J. QUIGG

*Attesting Officer*   *Commissioner of Patents and Trademarks*